United States Patent
Best et al.

(10) Patent No.: US 11,452,518 B2
(45) Date of Patent: Sep. 27, 2022

(54) CIRCULAR SUTURE CONSTRUCTS AND METHODS FOR USE

(71) Applicant: ARTHREX, INC., Naples, FL (US)

(72) Inventors: Joshua Best, Naples, FL (US); Tyler Esposito, Fort Myers, FL (US); Colin Baker, Naples, FL (US); Arley Perez, III, New Haven, CT (US)

(73) Assignee: Arthrex, Inc., Naples, FL (US)

( * ) Notice: Subject to any disclaimer, the term of this patent is extended or adjusted under 35 U.S.C. 154(b) by 592 days.

(21) Appl. No.: 16/406,428

(22) Filed: May 8, 2019

(65) Prior Publication Data

US 2019/0261978 A1    Aug. 29, 2019

Related U.S. Application Data

(63) Continuation of application No. 15/277,461, filed on Sep. 27, 2016, now Pat. No. 10,307,154.

(51) Int. Cl.
*A61B 17/04* (2006.01)
*A61B 17/06* (2006.01)

(52) U.S. Cl.
CPC ...... *A61B 17/0466* (2013.01); *A61B 17/0401* (2013.01); *A61B 2017/0404* (2013.01); *A61B 2017/0406* (2013.01); *A61B 2017/0417* (2013.01); *A61B 2017/0475* (2013.01); *A61B 2017/06185* (2013.01)

(58) Field of Classification Search
CPC ........... A61B 17/0401; A61B 17/0466; A61B 2017/0403; A61B 2017/0404; A61B 2017/0406; A61B 2017/0408; A61B 2017/0438; A61B 2017/06185; A61B 2017/0414; A61B 2017/0417; A61B 2017/0475; A61B 2017/042; A61B 2017/0464; A61B 2017/0477; A61F 2/10; A61F 2/105

See application file for complete search history.

(56) References Cited

U.S. PATENT DOCUMENTS

| | | | |
|---|---|---|---|
| 3,608,095 A | 9/1971 | Barry | |
| 5,064,431 A * | 11/1991 | Gilbertson | A61F 2/2445 623/2.37 |
| 5,989,252 A | 11/1999 | Fumex | |
| 6,511,498 B1 | 1/2003 | Fumex | |

(Continued)

FOREIGN PATENT DOCUMENTS

| | | |
|---|---|---|
| EP | 2098172 A1 | 9/2009 |
| EP | 2430984 A1 | 3/2012 |
| EP | 2698117 A1 | 2/2014 |

OTHER PUBLICATIONS

Cayenne Medical, CrossFix® II Meniscal Repair System, Surgical Technique Guide, 60284 Rev. C, four pages.

(Continued)

*Primary Examiner* — Dianne Dornbusch
(74) *Attorney, Agent, or Firm* — Carlson, Gaskey & Olds, P.C.

(57) ABSTRACT

A suture construct includes, inter alia, a sheath and a flexible strand threaded through the sheath to configure the sheath in a circular or oblong shape. The suture construct may be utilized in various tissue reconstruction procedures. The suture construct can be connected to a second suture construct to form a surgical assembly.

22 Claims, 8 Drawing Sheets

(56) References Cited

U.S. PATENT DOCUMENTS

| | | |
|---|---|---|
| 7,749,250 B2 | 7/2010 | Stone et al. |
| 8,273,106 B2 | 9/2012 | Stone et al. |
| 8,795,334 B2 | 8/2014 | Astorino et al. |
| 8,961,538 B2 | 2/2015 | Koogle, Jr. et al. |
| 9,314,241 B2 | 4/2016 | Stone et al. |
| 9,700,921 B2 | 7/2017 | Yao |
| 9,918,826 B2 | 3/2018 | Berelsman et al. |
| 2007/0185532 A1* | 8/2007 | Stone ............... A61B 17/0401 606/232 |
| 2008/0027446 A1 | 1/2008 | Stone et al. |
| 2008/0065114 A1 | 3/2008 | Stone et al. |
| 2008/0082127 A1 | 4/2008 | Stone et al. |
| 2008/0312689 A1 | 12/2008 | Denham et al. |
| 2009/0054928 A1 | 2/2009 | Denham et al. |
| 2009/0062854 A1 | 3/2009 | Kaiser et al. |
| 2009/0306711 A1 | 12/2009 | Stone et al. |
| 2009/0318961 A1 | 12/2009 | Stone et al. |
| 2011/0022083 A1 | 1/2011 | DiMatteo et al. |
| 2011/0098727 A1 | 4/2011 | Kaiser et al. |
| 2012/0059417 A1* | 3/2012 | Norton ............... A61B 17/1655 606/232 |
| 2012/0095470 A1 | 4/2012 | Kaiser et al. |
| 2012/0116450 A1 | 5/2012 | McDevitt et al. |
| 2012/0239085 A1 | 9/2012 | Schlotterback et al. |
| 2013/0116730 A1 | 5/2013 | Denham et al. |
| 2013/0123810 A1 | 5/2013 | Brown et al. |
| 2013/0144337 A1 | 6/2013 | Stone et al. |
| 2013/0296934 A1 | 11/2013 | Sengun |
| 2014/0052178 A1 | 2/2014 | Dooney, Jr. |
| 2014/0249577 A1 | 9/2014 | Pilgeram |
| 2017/0020655 A1 | 1/2017 | Dreyfuss et al. |

OTHER PUBLICATIONS

Biomet Sports Medicine, MaxFire MarXmen Meniscal Repair Device with Zip Loop Technology, Meniscal Repair, Surgical Protocol by Keith Lawhorn, M.D., sixteen pages.
Biomet Sports Medicine, MaxFire Meniscal Repair Device, Surgical Protocol written by Keith Lawhorn M.D., twelve pages.
DePuy Mitek Inc., Derek Ochiai, MD, Nirschl Orthopaedic Center, Arlington, VA, OMNISPAN™ Meniscal Repair Utilizing the CHIA PERCPASSER® Suture Passer, two pages.
Smith & Nephew Q-FIX All-Suture Implants, six pages.
Mitek Products, RapidLoc Meniscal Repair system, Surgical Technique for Repair of Maniscal Tears, two pages.
International Preliminary Report on Patentability for PCT Application No. PCT/US2017/052910 dated Apr. 11, 2019.
International Search Report and Written Opinion of the International Searching Authority for International Application No. PCT/US2017/052910 dated Nov. 17, 2017.

* cited by examiner

CIRCULAR SUTURE CONSTRUCTS AND METHODS FOR USE

RELATED APPLICATIONS

This application is a continuation of prior U.S. application Ser. No. 15/277,461, filed Sep. 27, 2016, now U.S. Pat. No. 10,307,154 granted Jun. 4, 2019, the entirety of which is herein incorporated by reference.

BACKGROUND

This disclosure relates to suture constructs and methods of using the suture constructs in various tissue reconstruction procedures.

Orthopedic procedures are often performed to repair musculoskeletal injuries. For example, soft tissue may tear away from bone during vigorous exercise or sporting activities. When tears occur, reattachment is often necessary to repair the damaged tissue. Suture anchors and buttons are two types of surgical devices that have been developed to facilitate these repairs; however, additional advancements in this field of technology are desired.

SUMMARY

This disclosure relates to suture constructs and methods of use. A suture construct may include a sheath and a flexible strand threaded through the sheath. Together, the sheath and the flexible strand form a "soft" suture construct. The suture constructs can be used in various tissue reconstruction procedures, including but not limited to, ACL/PCL reconstructions and meniscal tear repairs.

A suture construct according to an exemplary aspect of this disclosure includes, inter alia, a sheath and a flexible strand threaded through the sheath to establish a bridge configuration that includes at least two stand portions that cross over one another outside of the sheath.

A method according to another exemplary aspect of this disclosure includes, inter alia, utilizing a suture construct in a tissue reconstruction procedure. The suture construct includes a sheath and a flexible strand threaded through the sheath to configure the sheath in a circular or oblong shape.

A surgical assembly according to yet another exemplary aspect of this disclosure includes, inter alia, a first suture construct, a second suture construct, and a flexible strand that connects the first suture construct to the second suture construct. The flexible strand includes a sliding knot.

DETAILED DESCRIPTION

Figure 1:
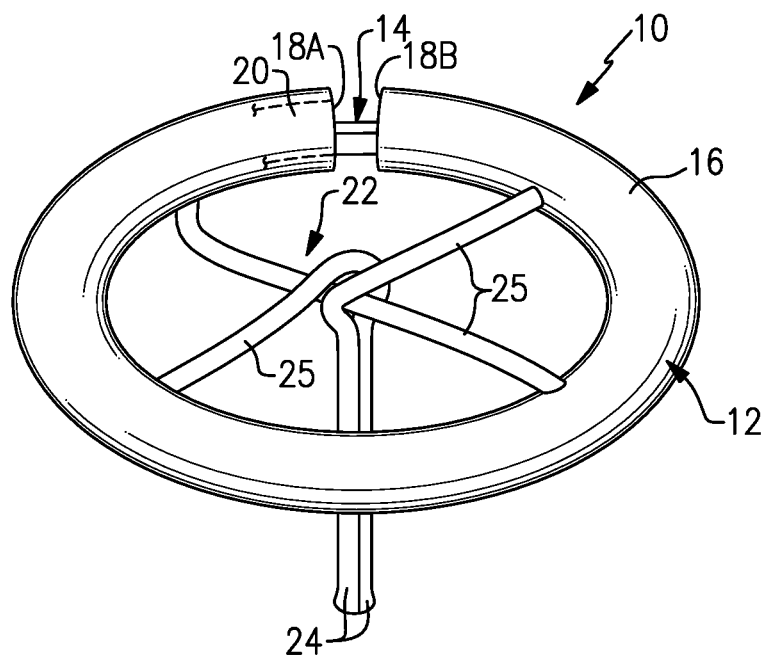
FIG. 1 illustrates a suture construct according to a first embodiment of this disclosure.

This disclosure relates to suture constructs and their related methods of use. A suture construct can include a sheath and a flexible strand threaded through the sheath to form a "soft" suture construct. The suture constructs can be used in various tissue reconstruction procedures, including but not limited to, ACL/PCL reconstructions and meniscal tear repairs.

A suture construct according to an exemplary aspect of this disclosure includes, inter alia, a sheath and a flexible strand threaded through the sheath to establish a bridge configuration that includes at least two stand portions that cross over one another outside of the sheath.

In a further embodiment, a sheath includes a tubular body that extends between a first open end and a second open end.

In a further embodiment, a second open end of a sheath is adjacent to and faces a first open end when a sheath is configured in a circular or oblong shape.

In a further embodiment, a flexible strand of a suture construct exits through a sheath at multiple splice points.

In a further embodiment, a flexible strand establishes a bridge configuration inside a perimeter of a circular or oblong shape of a sheath of a suture construct.

In a further embodiment, a bridge configuration is a double bridge configuration.

In a further embodiment, a double bridge configuration includes multiple strand portions of a flexible strand exiting through multiple splice points of a sheath.

In a further embodiment, a second suture construct is connected to a suture construct.

In a further embodiment, a flexible strand of a suture construct or a second flexible strand of a second suture construct connects the suture construct and the second suture construct.

In a further embodiment, a sliding knot is formed in a flexible strand.

In a further embodiment, a flexible strand is threaded through opposing ends and at least four splice points of a sheath.

In a further embodiment, a sheath and a flexible strand are both made exclusively of soft, suture based materials.

In a further embodiment, a flexible strand includes a first strand portion that extends outside of a sheath and connects between opposing splice points of the sheath.

In a further embodiment, a second strand portion crosses over a first strand portion to establish an X-shaped bridge configuration.

A method according to another exemplary aspect of this disclosure includes, inter alia, utilizing a suture construct in a tissue reconstruction procedure. The suture construct includes a sheath and a flexible strand threaded through the sheath to configure the sheath in a circular or oblong shape.

In a further embodiment, a sheath is configured in a circular shape prior to utilizing a suture construct in a tissue reconstruction procedure.

In a further embodiment, a tissue reconstruction procedure is an ACL reconstruction procedure.

In a further embodiment, the ACL reconstruction procedure includes attaching a flexible strand to a graft, and suspending the graft within a bone tunnel with a suture construct.

In a further embodiment, a tissue reconstruction procedure is a meniscal tear repair procedure.

A surgical assembly according to yet another exemplary aspect of this disclosure includes, inter alia, a first suture construct, a second suture construct, and a flexible strand that connects the first suture construct to the second suture construct. The flexible strand includes a sliding knot.

Figure 2:
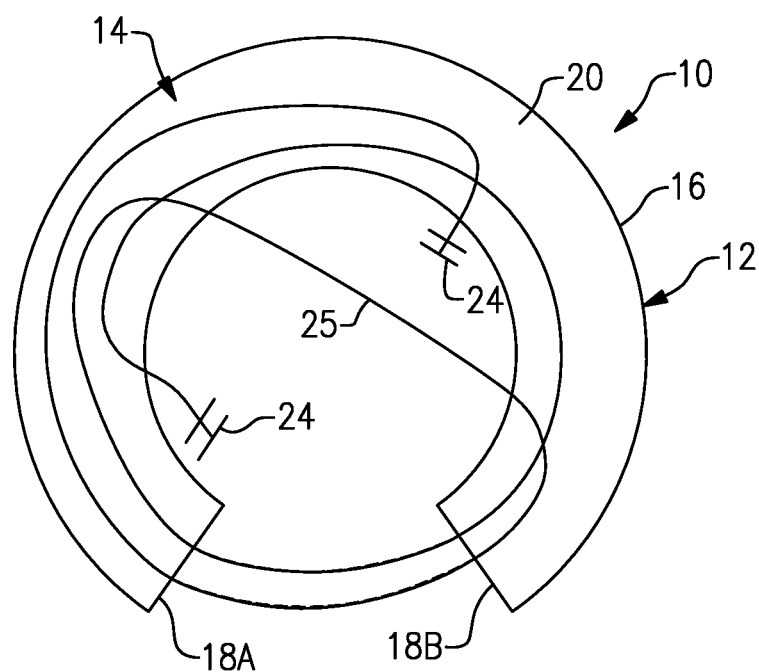
FIG. 2 is a cross-sectional view of the suture construct of FIG. 1.

FIGS. 1 and 2 illustrate a suture construct 10. The suture construct 10 is configured for use in various tissue reconstruction procedures and may be fixated within a joint to repair torn tissue. ACL/PCL reconstructions and meniscal tear repairs are but two non-limiting examples of tissue reconstruction procedures which could benefit from the suture constructs of this disclosure.

The suture construct 10 may be referred to as a "soft" construct because it is formed of soft materials such as yarns, fibers, filaments, strings, fibrils, strands, sutures, etc., or any combination of such materials. The soft materials may be synthetic or natural materials, or combinations of synthetic and nature materials, and may be biodegradable or non-biodegradable within the scope of this disclosure. In an embodiment, the suture construct 10 is made exclusively of soft, suture based materials. The soft materials confer the ability to be inserted into or through tissue (e.g., bone, ligament, tendon, etc.) and then bunch together, collapse, expand and/or change shape to fixate the suture construct 10 relative to the tissue.

The exemplary suture construct 10 may include a sheath 12 and a flexible strand 14 that is threaded through the sheath 12 in a manner that configures the sheath 12 in a circular or oblong shape. The sheath 12 is configured in the circular or oblong shape in its non-deployed state. Stated another way, the circular or oblong shape is formed before using the suture construct 10 in a tissue reconstruction procedure, or before the suture construct 10 has been bunched together (i.e., deployed) by tensioning the flexible strand 14.

The sheath 12 includes a tubular body 16 that extends between opposing ends 18A, 18B. The opposing ends 18A, 18B may be open ends. In one example shown in FIG. 1, the first open end 18A of the sheath 12 is not attached and not connected to the second open end 18B of the sheath 12. The tubular body 16 established a bore 20 that extends between the opposing ends 18A, 18B for accommodating the flexible strand 14. When positioned in the circular or oblong shape, the opposing ends 18A, 18B of the sheath 12 are adjacent and may be parallel to one another. In one example shown in FIG. 1, the sheath 12 defines a single channel.

In an embodiment, the sheath 12 is a tubular sleeve made of a flexible material, such as a braided, woven, or knitted structure made of yarns, fibers, filaments, sutures, or other similar materials, or combinations of these materials. In another embodiment, the sheath 12 is constructed of polyester suture material. However, other flexible materials may also be suitable for constructing the sheath 12.

The flexible strand 14 is passed through the bore 20 of the sheath 12. The flexible strand 14 can be threaded through the bore 20 in one or more passes to configure the sheath 12 in a circular or oblong shape in its non-deployed state. The flexible strand 14 may also be tensioned to assist in deploying the sheath 12 after inserting the suture construct 10 into or through tissue.

In another embodiment, the flexible strand 14 may exit the tubular body 16 through a plurality of splice points of the tubular body 16. The splice points are spaced from the opposing ends 18A, 18B of the sheath 12. The flexible strand 14 may include one or more strand portions 25 that extend outside of the sheath 12 and connect between opposing splice points. In an embodiment, the strand portions 25 establish a bridge configuration 22 within the center space/opening that is formed by configuring the sheath 12 in the circular or oblong shape. The flexible strand 14 may include any length and also includes free ends 24 that extend from the bridge configuration 22 outside of the bore 20 of the sheath 12. In an embodiment, at least a portion of the strand portions 25 cross over one another to establish an X-shaped bridge configuration 22. The sheath 12 defines a perimeter, and the first strand portion 25 crosses over the second strand 25 portion to establish the bridge configuration 22 at a location substantially in a center of a space defined by the perimeter of the sheath 12 when the sheath 12 is in the non-deployed state.

In an embodiment, the flexible strand 14 is a suture. Non-limiting examples of suitable sutures include FiberWire®, TigerWire®, or FiberChain® suture, which are each available from Arthrex, Inc., although any type of suture may be utilized, including cored or coreless sutures. In another embodiment, the flexible strand 14 is flat suture, such as FiberTape® or SutureTape®, which are also available from Arthrex, Inc. The flexible strand 14 could include any soft, flexible strand of material.

Figure 3:
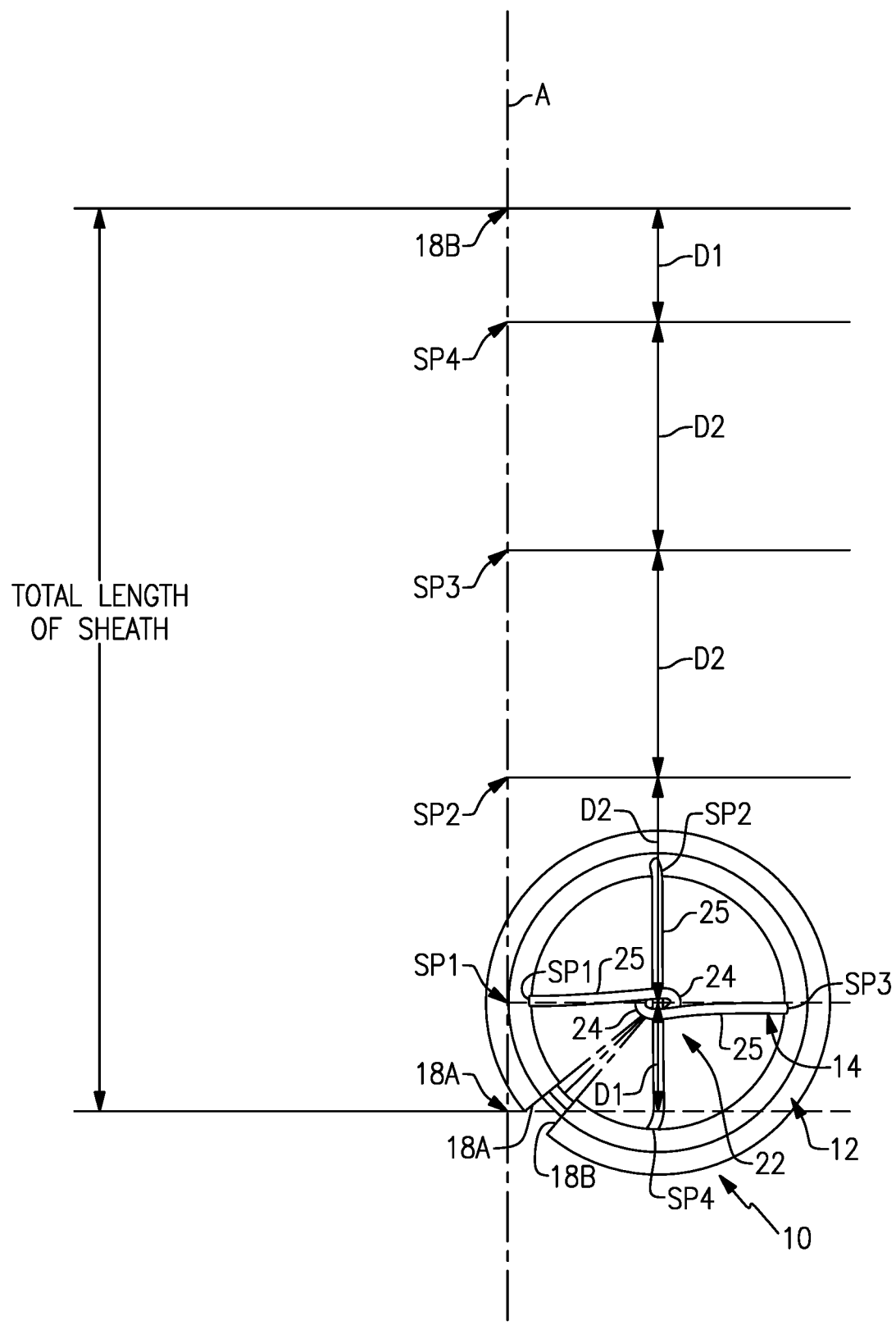
FIG. 3 schematically illustrates a method of constructing the suture construct of FIGS. 1 and 2.

FIG. 3, with continued reference to FIGS. 1-2, illustrates a method of constructing the suture construct 10. In addition to threading the flexible strand 14 through the opposing ends 18A, 18B of the sheath 12, the flexible strand 14 may be threaded through a plurality of splice points SP1, SP2, SP3, and SP4. The splice points SP1, SP2, SP3, and SP4 are located in sequential order moving in a clockwise direction from the opposing end 18A toward the opposing end 18B of the sheath 12.

An exemplary spacing between the splice points SP1, SP2, SP3, and SP4 and between the opposing ends 18A, 18B and the splice points SP1 and SP4, respectively, is shown in FIG. 3. To better illustrate the exemplary spacing, the splice points SP1, SP2, SP3, and SP4 are depicted along a linear axis A in addition to their depiction relative to the circular or oblong shaped suture construct 10. The linear axis A represents a longitudinal axis of the sheath 12 in its straightened configuration (i.e., before configuring the sheath 12 in the circular or oblong shape). In an embodiment, the splice point SP1 and the splice point SP4 are spaced a first distance D1 from the opposing end 18A and the opposing end 18B, respectively. In another embodiment, a second distance D2 is provided between splice points SP1 and SP2, between splice points SP2 and SP3, and between splice points SP3 and SP4. The second distance D2 may be larger than the first distance D1, in yet another embodiment. The actual spacing between the splice points SP1, SP2, SP3, and SP4 may vary depending on the size of the sheath 12 and the type of reconstruction procedure the suture construct 10 is being used for, among other design criteria. In one example shown in FIG. 3, the first splice point SP1 and the third splice point SP3 are located on opposing sides of the sheath 12.

In an embodiment, the flexible strand 14 is threaded through the sheath 12 as follows in order to configure the suture construct 10 in the circular or oblong shape:

Step 1: Insert a first free end of the free ends 24 of the flexible strand 14 through the opposing end 18B of the sheath 12 and then move the flexible strand 14 in a counterclockwise direction through the bore 20 of the sheath 12. Exit the flexible strand 14 from the sheath 12 through the splice point SP1.

Step 2: Insert a second free end of the free ends 24 of the flexible strand 14 through the opposing end 18A of the sheath 12 and then move the flexible strand 14 in a clockwise direction through the bore 20 of the sheath 12. Exit the flexible strand 14 from the sheath 12 through the splice point SP2.

Step 3: Insert the strand portion 25 of the flexible strand 14 exiting splice point SP2 through the splice point SP4 and reenter the bore 20 of the sheath 12. Next, move the flexible strand 14 in a clockwise direction until it exits through the opposing end 18B.

Step 4: Insert the flexible strand 14 back through the opposing end 18A and then exit the flexible strand 14 through the splice point SP3.

Step 5: Tension the free ends 24 of the flexible strand 14 that exit from the splice points SP1 and SP3 to configure the sheath 12 in the circular or oblong shape. The opposing ends 18A, 18B are directly adjacent one another and face one another when the sheath 12 is positioned in the circular or oblong shape.

Step 6: Route the free ends 24 of the flexible strand 14 that exit from the splice points SP1 and SP3 around the strand portion 25 of the flexible strand 14 extending between the splice points SP2 and SP4 to establish an "X" shaped bridge configuration 22 inside a perimeter of the circular or oblong shaped sheath 12.

Step 7: Splice the free ends 24 of the flexible strand 14 together, such as by tying the free ends 24 together using a knot. If necessary, the free ends 24 of the flexible strand 14 can be tipped with a suitable material to avoid fraying.

Figure 4:
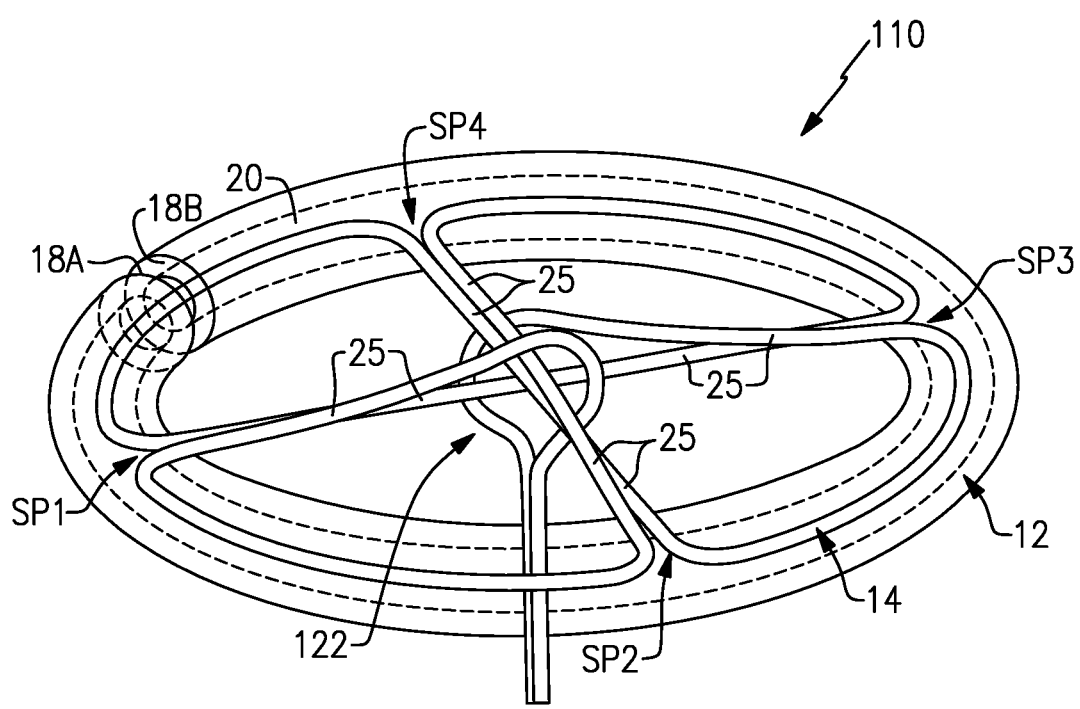
FIG. 4 illustrates a suture construct according to a second embodiment of this disclosure.

FIG. 4 illustrates another exemplary embodiment of a suture construct 110. In this disclosure, like reference numerals designate like elements where appropriate and reference numerals with the addition of 100 or multiples thereof designate modified elements that are understood to incorporate the same features and benefits of the corresponding original elements. The suture construct 110 includes a sheath 12 and a flexible strand 14 threaded through the sheath 12. The sheath 12 is shown as slightly transparent in FIG. 4 to better illustrate how the flexible strand 14 is threaded through the sheath 12.

The flexible strand 14 is threaded through the sheath 12 to configure the sheath 12 in a circular or oblong shape. The suture construct 110 of FIG. 4 is similar to the suture construct 10 of FIGS. 1-3. However, in this embodiment, the flexible strand 14 is threaded though the sheath 12 to establish a double bridge configuration 122 in the center of the circular or oblong shaped sheath 12. In the double bridge configuration 122, two strand portions 25 of the flexible strand 14 exit the sheath 12 through each splice point SP1, SP2, SP3, and SP4.

Figure 5:
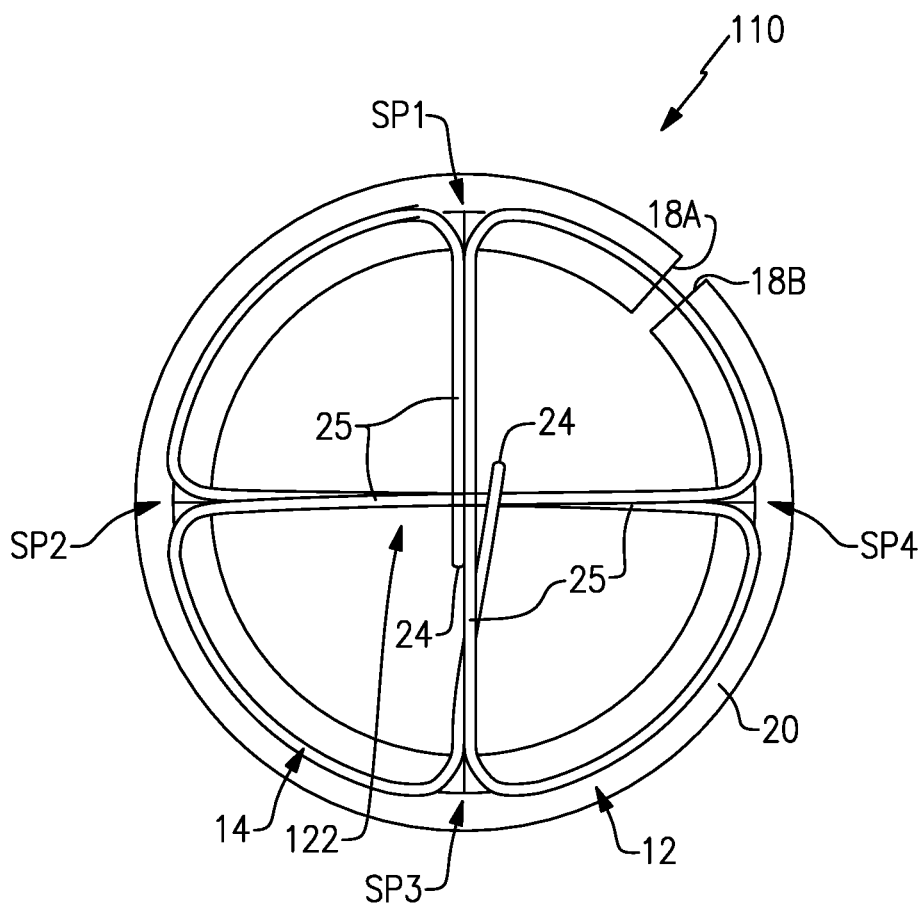
FIG. 5 schematically illustrates a method of constructing the suture construct of FIG. 4.

FIG. 5, with continued reference to FIG. 4, schematically illustrates a manner in which the flexible strand 14 can be threaded through the sheath 12 to construct the suture construct 110 that includes the double bridge configuration 122. In an embodiment, the flexible strand 14 is threaded through the sheath 12 as follows to construct the suture construct 110:

Step 1: Insert a first free end of the free ends 24 of the flexible strand 14 through the splice point SP1 and then move the flexible strand 14 in a counterclockwise direction through a bore 20 of the sheath 12. Exit the flexible strand 14 from the sheath 12 through the splice point SP2.

Step 2: Insert the strand portion 25 of the flexible strand 14 exiting the splice point SP2 through the splice point SP4 and then exit the flexible strand 14 from the sheath 12 through the splice point SP3.

Step 3: Insert the strand portion 25 of the flexible strand 14 exiting the splice point SP3 back through the splice point SP1 and then exit the flexible strand 14 from the sheath 12 through the opposing end 18A.

Step 4: Insert the flexible strand 14 through the opposing end 18B and then exit the flexible strand 14 back through the splice point SP4.

Step 5: Insert the strand portion 25 of the flexible strand 14 exiting the splice point SP4 back through the splice point SP2 and then exit the flexible strand 14 back through the splice point SP3.

Step 6: Tension the free ends 24 of the flexible strand 14 that exit from the splice points SP1 and SP3 to configure the sheath 12 in the circular or oblong shape. The opposing ends 18A, 18B are directly adjacent one another and face one another when the sheath 12 is positioned in the circular shape.

Step 6: Route the free ends 24 of the flexible strand 14 that exit from the splice points SP1 and SP3 around the strand portions 25 of the flexible strand 14 extending between the splice points SP2 and SP4 to establish an "X" shaped double bridge configuration 122 inside a perimeter of the circular or oblong shaped sheath 12.

Step 7: Splice the free ends 24 of the flexible strand 14 together, such as by tying or stitching the free ends 24 of the flexible strand 14 together.

Figure 6:
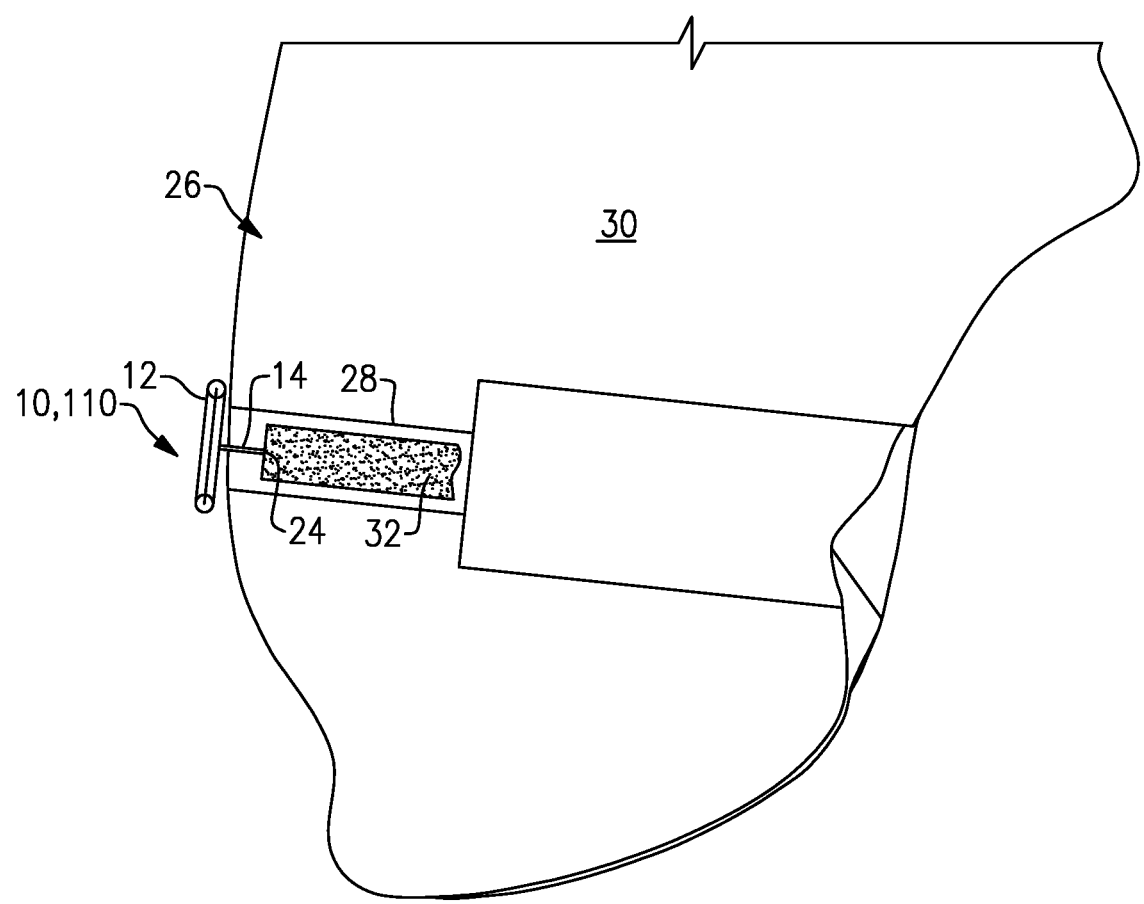
FIG. 6 schematically illustrates a method of using a suture construct as part of a tissue reconstruction procedure.

FIG. 6 illustrates an exemplary surgical use of the suture construct 10 (or suture construct 110) during a tissue reconstruction procedure, such as an ACL reconstruction procedure. However, it should be understood that this disclosure is not limited to ACL reconstruction procedures, and the suture constructs of this disclosure could be used in a variety of tissue repair or reconstruction procedures within the scope of this disclosure.

The suture construct 10, 110 may be implanted within a joint 26 (e.g., a knee joint) to repair a torn tissue (e.g., a torn ACL). Prior to positioning the suture construct 10 within the joint 26, a bone tunnel 28 (i.e., a socket, hole, opening, etc.) is formed in a bone 30 (e.g., a femur). The bone tunnel 28 may be formed using known drilling techniques to establish voids within the bone 30 for accommodating the suture construct 10, 110. In an embodiment, the sheath 12 of the suture construct 10, 110 is already configured in a circular or oblong shape prior to implantation of the suture construct 10 within the joint 26. Thus, the suture construct 10, 110 is configured in the circular or oblong shape in what is referred to as its pre-deployed state. In another embodiment, the suture construct 10, 110 is deployed into the joint 26 in a straight configuration (e.g., the sheath 12 is generally straight along linear axis A) and can then be tensioned into the circular or oblong shape by pulling on the free ends 24.

In an exemplary embodiment, the suture construct 10 is implanted by passing the suture construct 10, 110 through the bone tunnel 28. The suture construct 10, 110 may be pushed or pulled through the bone tunnel 28.

The free ends 24 of the flexible strand 14 of the suture construct 10, 110 may be attached to a graft 32. Therefore, once the suture construct 10, 110 is implanted within the joint 26, the graft 32 is suspended within the bone tunnel 28 to reconstruct or repair the ACL. Fixation of the graft 32 to a second bone (not shown), such as a tibia, can be achieved using known techniques. The graft 32 may be tensioned to tension the flexible strand 14 and thereby cause the suture construct 10, 110 to bunch up and thus, collapse, expand, and/or change shape to fixate relative to the bone tunnel 28 of the bone 30.

Figure 7:
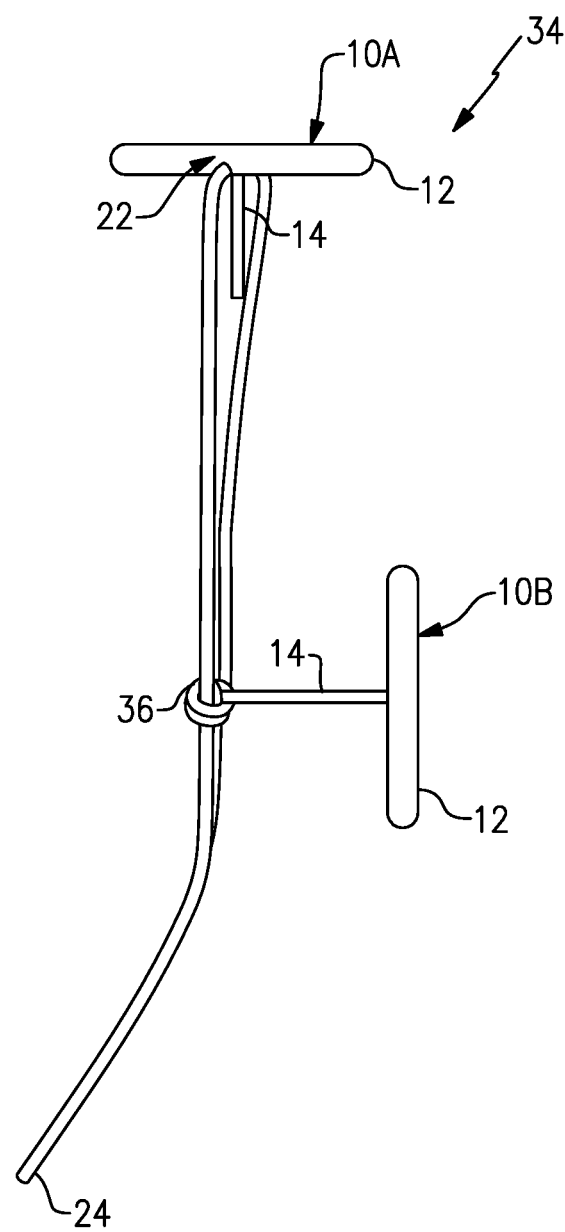
FIG. 7 illustrates a surgical assembly that includes a first suture construct and a second suture construct.

FIG. 7 illustrates a surgical assembly 34 that includes a first suture construct 10A and a second suture construct 10B. Although depicted including suture constructs similar to those of FIGS. 1-3, the surgical assembly 34 could also be made up of suture constructs 110 of FIGS. 4-5, or a combination of the suture construct 10 of FIGS. 1-3 and the suture construct 110 of FIGS. 4-5.

Each suture construct 10A, 10B includes a sheath 12 and a flexible strand 14. The flexible strands 14 are threaded through the sheaths 12 to configure the sheaths 12 in a circular or oblong shape. In an embodiment, the first suture construct 10A is connected to the second suture construct 10B by a flexible strand, such as the flexible strand 14 of the second suture construct 10B. For example, the free end 24 of the flexible strand 14 of the second suture construct 10B may be looped over the bridge configuration 22 of the first suture construct 10A to connect the first and second suture constructs 10A, 10B.

The flexible strand 14 that connects the first and second suture constructs 10A, 10B may include a sliding knot 36. The sliding knot 36 can be adjusted to alter the amount of slack between the first suture construct 10A and the second suture construct 10B and thus close a tissue tear, as discussed in greater detail below.

Figure 8:
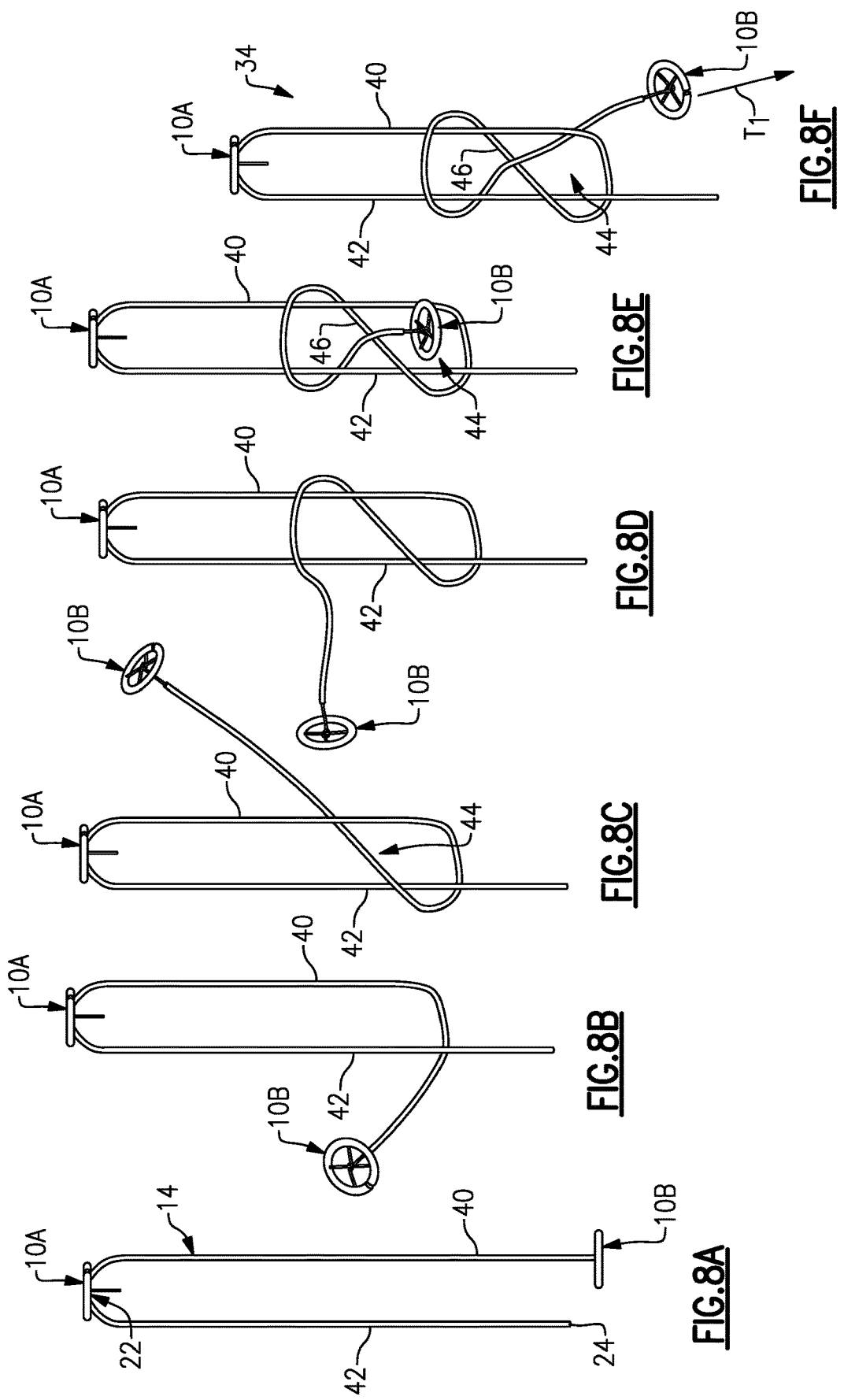
FIGS. 8A-8F schematically illustrate a method of constructing the surgical assembly of FIG. 7.

FIGS. 8A-8F schematically illustrate a method for constructing the surgical assembly 34 of FIG. 7. Referring first to FIG. 8A, the free end 24 of the flexible strand 14 of the second suture construct 10B is looped over the bridge configuration 22 of the first suture construct 10A. The flexible strand 14 of the second suture construct 10B may be longer than the flexible strand 14 of the first suture construct 10A in order to provide a sufficient length to use the flexible strand 14 of the second suture construct 10B for connecting the first and second suture constructs 10A, 10B. Looping the flexible strand 14 of the second suture construct 10B in this manner creates a right tail lead portion 40 and a post portion 42 in the flexible strand 14 of the second suture construct 10B.

Next, the right tail lead portion 40 is wrapped under the post portion 42 (see FIG. 8B). The second suture construct 10B is then wrapped over the post portion 42, through an opening 44 between the post portion 42 and the right tail lead portion 40, and then under the right tail lead portion 40 (see FIG. 8C). The second suture construct 10B is then wrapped around both the right tail lead portion 40 and the post portion 42 (see FIG. 8D).

As shown in FIG. 8E, the second suture construct 10B is next wrapped under the post portion 42 back toward the opening 44 and over a crossed lead 46. Finally, as shown in FIG. 8F, the second suture construct 10B is placed through the opening 44 and back under the right tail lead portion 40. The second suture construct 10B may be further tensioned in the direction T1 to fully form the sliding knot 36 shown in FIG. 7.

Figure 9:
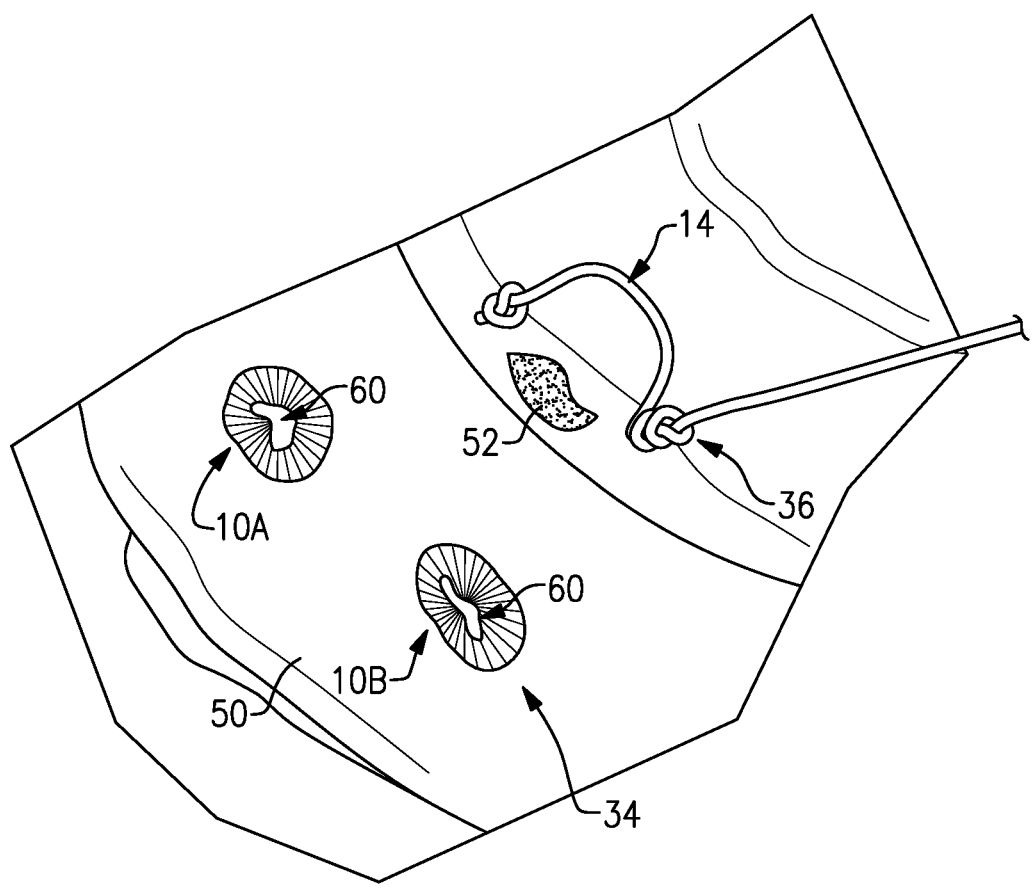
FIG. 9 schematically illustrates a method of using a surgical assembly of suture constructs as part of a tissue reconstruction procedure.

FIG. 9, with continued reference to FIGS. 7 and 8A-8F, illustrates an exemplary surgical use of the surgical assembly 34 during a tissue reconstruction procedure, such as a meniscal tear repair procedure. For example, the surgical assembly 34 may be inserted through a meniscus 50 to repair a meniscus tear 52. The first suture construct 10A is inserted through the meniscus 50 first, and then the second suture construct 10B is inserted through the meniscus 50 at an adjacent location. Once inserted, the flexible strand 14 that connects the first and second suture constructs 10A, 10B is positioned on an opposite side of the meniscus 50 from the first and second suture constructs 10A, 10B.

The sliding knot 36 formed in the flexible strand 14 may then be moved to tension the flexible strand 14 and close the tear 52. In an embodiment, a knot pusher is used to advance the sliding knot 36. As the sliding knot 36 is advanced and tension accumulates in the flexible strand 14, the first and second suture constructs 10A, 10B bunch together to form anchoring clusters 60. The anchoring clusters 60 promote fixation of the surgical assembly 34 relative to the meniscus 50 and facilitate closing of the tear 52.

The suture constructs of this disclosure provide increased bulkiness and rigidity and therefore exhibit increased pull-out strength compared to prior art constructs. The circular or oblong shape of the suture constructs of this disclosure maximizes the amount of construct retention surface area achieved during construct deployment.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A suture construct, comprising:
a sheath including a tubular body having a first open end, a second open end, a first splice point, a second splice point, a third splice point, a non-deployed state, and a deployed state, wherein the sheath is configured in a circular shape when in the non-deployed state, the first open end faces and is adjacent to the second open end, the first open end is substantially parallel to the second open end, and the sheath defines a perimeter; and
a flexible strand threaded through the sheath to establish a bridge configuration, the flexible strand including a first strand portion having a first free end that extends through the first splice point of the sheath and a second strand portion that extends through the second splice point and through the third splice point, and the first strand portion crosses over the second strand portion outside of the sheath to establish the bridge configuration, and the first strand portion crosses over the second strand portion to establish the bridge configuration at a location substantially in a center of a space defined by the perimeter when the sheath is in the non-deployed state.

2. The suture construct as recited in claim 1, wherein the first open end of the sheath is not attached to the second open end of the sheath.

3. The suture construct as recited in claim 1, wherein the first splice point and the third splice point are located on opposing sides of the sheath when in the non-deployed state.

4. The suture construct as recited in claim 1, wherein the sheath defines a single channel.

5. A suture construct, comprising:
a sheath including a tubular body having a first open end, a second open end, a first splice point, second splice point, a non-deployed state, and a deployed state wherein the first open end faces and is adjacent to the second open end, the first open end is substantially parallel to the second open end, and the sheath defines a perimeter; and
a flexible strand threaded through the sheath to establish a bridge configuration, wherein the flexible strand includes a first strand portion having a first free end outside the sheath, a second strand portion having a second free end outside the sheath, the first strand portion extends through the first splice point of the sheath, and the second strand portion extends through the second splice point of the sheath, and the first strand portion crosses over the second strand portion to establish the bridge configuration at a location substantially in a center of a space defined by the perimeter when the sheath is in the non-deployed state.

6. The suture construct as recited in claim 5, wherein the sheath is configured in a circular or oblong shape.

7. The suture construct as recited in claim 5, wherein the first splice point is spaced from the second splice point along the tubular body of the sheath.

8. The suture construct as recited in claim 5, wherein the bridge configuration is an X-shaped bridge configuration.

9. The suture construct as recited in claim 5, wherein the bridge construction is a double bridge construction.

10. The suture construct as recited in claim 5, wherein flexible strand includes another strand portion that extends between the first open end to the second open end.

11. The suture construct as recited in claim 5, wherein the first open end and the second open end are substantially flat.

12. The suture construct as recited in claim 5, wherein the flexible strand includes a third strand portion, and the first strand portion and the third strand portion cross over the second strand portion outside of the sheath to establish the bridge configuration, wherein the third strand portion exits the sheath through a third splice point.

13. The suture construct as recited in claim 12, wherein the bridge construction is a double bridge construction such that each of the first strand portion, the second strand portion, and the third strand portion is a double strand portion, and the double bridge configuration includes the first strand portion that exits the sheath through the first splice point, the third strand portion that exits the sheath through the third splice point, and the second strand portion that exits the sheath through a second splice point and a fourth splice point.

14. The suture construct as recited in claim 13, wherein the first strand portion and the third strand portion are substantially perpendicular to the second strand portion.

15. The suture construct as recited in claim 12, wherein the first strand portion and the third strand portion are substantially perpendicular to the second strand portion.

16. The suture construct as recited in claim 12, wherein the sheath includes a fourth splice point, and the second strand portion extends through the second splice point and the fourth splice point.

17. The suture construct as recited in claim 16, wherein the sheath is configured in a circular shape, and the first splice point, the second splice point, the third splice point, and the fourth splice point are equally spaced around the circle.

18. The suture construct as recited in claim 12, wherein the first splice point and the third splice point are located on opposing sides of the sheath.

19. The suture construct as recited in claim 5, including a second suture construct connected to the suture construct, wherein the flexible strand of the suture construct or a second flexible strand of the second suture construct connects the suture construct and the second suture construct.

20. The suture construct as recited in claim 19, including a sliding knot formed in the flexible strand or the second flexible strand.

21. The suture construct as recited in claim 5, wherein the first open end of the sheath is not attached to the second open end of the sheath.

22. The suture construct as recited in claim 5, wherein the sheath defines a single channel when in the non-deployed state.

* * * * *